United States Patent [19]
Kubiak et al.

[11] Patent Number: 6,004,025
[45] Date of Patent: Dec. 21, 1999

[54] AUTOMATED LIQUID MANUFACTURING SYSTEM

[75] Inventors: James M. Kubiak, Depew; Todd A. Battistoni, Clarence; David W. Jayme, Grand Island, all of N.Y.

[73] Assignee: Life Technologies, Inc., Rockville, Md.

[21] Appl. No.: 08/857,496

[22] Filed: May 16, 1997

[51] Int. Cl.⁶ ..................................................... B01F 15/02
[52] U.S. Cl. .................................... 366/173.1; 366/175.2; 366/181.4
[58] Field of Search ............................. 366/152.4, 173.1, 366/174.1, 177.1, 178.1, 179.1, 181.8, 182.2, 181.5, 336, 339, 340; 422/189, 193, 194, 196; 137/5

[56] References Cited

U.S. PATENT DOCUMENTS

| | | | |
|---|---|---|---|
| 2,307,509 | 1/1943 | Joachim et al. | 366/178.2 |
| 3,692,283 | 9/1972 | Sauer et al. | 366/173.1 |
| 3,779,518 | 12/1973 | Koepke et al. | 366/174.1 |
| 4,019,983 | 4/1977 | Mandt | 210/62 |
| 4,051,065 | 9/1977 | Venema . | |
| 4,212,545 | 7/1980 | Lovasz et al. | 366/152.4 |
| 4,332,483 | 6/1982 | Hope et al. | 366/174.1 |
| 4,474,476 | 10/1984 | Tomsen | 366/152.4 |
| 4,549,813 | 10/1985 | Volz et al. | 366/160 |
| 4,737,349 | 4/1988 | Arnold et al. | 366/174.1 |
| 4,869,595 | 9/1989 | Lang | 366/137 |
| 5,205,647 | 4/1993 | Ricciardi | 366/176 |
| 5,324,109 | 6/1994 | Johari | 366/151 |
| 5,331,364 | 7/1994 | Borden | 354/324 |
| 5,474,931 | 12/1995 | DiSorbo et al. | 435/240.31 |
| 5,641,410 | 6/1997 | Peltzer | 366/152.4 |

FOREIGN PATENT DOCUMENTS

| | | |
|---|---|---|
| 0 473 356 A1 | 3/1992 | European Pat. Off. . |
| 42 00 720 A1 | 7/1993 | Germany . |
| 2 116 058 | 9/1983 | United Kingdom . |

OTHER PUBLICATIONS

"Continuous, high capacity reconstitution of nutrient media from concentrated intermediates," Cytotechnology, vol. 22, pp. 255–261, 1996, Kluwer Academic Publishers, The Netherlands, David W. Jayme, James M. Kubiak, Todd A. Battistoni, David J. Cady.

"Use of Liquid Medium Concentrates to Enhance Biological Productivity," Animal Cell Technology: Basic & Applied Aspects, vol. 5, pp. 215–222, 1993, David W. Jayme, Richard M. Fike, James M. Kubiak, Cheryl R. Nash, Paul J. Price.

"Use of Medium Concentrates To Improve Bioreactor Productivity," Animal Cell Technology: Basic & Applied Aspects, vol. 4, pp. 143–148, 1992, David W. Jayme, Dennis M. Disorbo, James M. Kubiak, Richard M. Fike.

"High Capacity Method For Producing Nutrient Medium From Concentrated Intermediates For Cell Culture Bioproduction Applications," The 1995 Annual Meeting of The Japanese Association of Animal Cell Technology, Japan, David W. Jayme, James M. Kubiak, Todd A. Battistoni, David J. Cady, Richard M. Fike.

"An Automated System to Produce Cell Culture Media from Liquid Medium Concentrates," BioPharm, vol. 8, No. 9, Nov. 1995, Advanstar Publication, Georg Roth, James M. Kubiak, James F. Long, Gary M. Schoofs.

*Primary Examiner*—Tony G. Soohoo
*Attorney, Agent, or Firm*—Sterne, Kessler, Goldstein & Fox, P.L.L.C.

[57] ABSTRACT

A method for continuously preparing a medium formulation mixes a diluent with a plurality of chemically incompatible concentrate solutions in such a manner that none of the ingredients of the concentrate solutions chemically react in an adverse manner The method utilizes a static mixing chamber to add the concentrate solutions to the diluent stream sufficiently in advance of one another so that adverse chemical reactions do not occur. The method also adjusts a pH level of the diluent prior to adding any of the concentrate solutions to the diluent.

25 Claims, 8 Drawing Sheets

AUTOMATED LIQUID MANUFACTURING SYSTEM

BACKGROUND OF THE INVENTION

1. Field of the Invention

The present invention relates to the field of cell culture medium formulations, and more specifically, to methods for continuously preparing cell culture medium formulations and buffered salt solutions from selected subgroups of medium concentrates.

2. Related Art

Cell culture medium formulation provide nutrients necessary to maintain and grow cells in a controlled, artificial and in vitro environment. Characteristics and compositions of the cell culture mediums vary depending on the particular cellular requirements. Important parameters include osmolarity, pH, and nutrient formulations.

Medium formulations have been used to grow a number of cell types including animal, plant and bacterial cells. Cells grown in culture medium catabolize available nutrients and produce useful biological substances such as monoclonal antibodies, hormones, growth factors and the like. Such products have therapeutic applications and, with the advent of recombinant DNA technology, cells can be engineered to produce large quantities of these products. Thus, the ability to grow cells in vitro is not only important for the study of cell physiology, it is necessary for the production of useful substances which may not otherwise be obtained by cost-effective means.

Cell culture medium formulations have been well documented in the literature and a number of medium are commercially available. Typical nutrients in cell culture medium formulations include amino acids, salts, vitamins, trace metals, sugars, lipids and nucleic acids. Often, particularly in complex medium formulations, stability problems result in toxic products and/or lower effective concentrations of required nutrients, thereby limiting the functional life-span of the culture medium. For instance, glutamine is a constituent of almost all medium formulations that are used in the culturing of mammalian cells in vitro. Glutamine decomposes spontaneously into pyrrolidone carboxylic acid and ammonia. The rate of degradation can be influenced by pH and ionic conditions but in cell culture medium, formation of these breakdown products cannot be avoided (Tritsch et al., *Exp. Cell Research,* 28:360–364(1962)).

Wang et al. (*In Vitro,* 14:(8):715–722 (1978)) have shown that photoproducts such as hydrogen peroxide, which are lethal to cells, are produced in Dulbecco's Modified Eagle's Medium (DMEM). Riboflavin and tryptophan or tyrosine are components necessary for formation of hydrogen peroxide during light exposure. Because most mammalian culture medium formulations contain riboflavin, tyrosine and tryptophan, toxic photoproducts are likely produced in most cell culture mediums.

To avoid these problems, researchers make medium formulations on an "as needed" basis, and avoid long term storage of the culture medium. Commercially available medium formulations, typically in dry powder form, serve as a convenient alternative to making the medium formulations from scratch, i.e., adding each nutrient individually, and also avoids some of the stability problems associated with liquid medium formulations. However, only a limited number of commercial culture medium formulations are available, except for those custom formulations supplied by the manufacturer.

Although dry powder medium formulations may increase the shelf-life of some medium formulations, there are a number of problems associated with dry powdered medium formulations, especially in large scale application. Production of large volumes requires storage facilities for the dry powder, not to mention the specialized kitchens necessary to mix and weigh the nutrient components. Due to the corrosive nature of dry powder medium ingredients, mixing tanks must be periodically replaced.

There exists a need to lower the cost of production of biological substances. Efficient and cost effective methods to stabilize liquid cell culture medium formulations as well as the development of convenient methods to produce 1x medium formulations would be an important development in the field of cell culture medium technology.

One such development in the field of cell culture medium formulations is the development of liquid medium concentrates as is disclosed in U.S. Pat. No. 5,474,931 issued to DiSorbo et al. on Dec. 12, 1995 ("DiSorbo"). DiSorbo discloses a method of subgrouping medium formulations into stable, compatible components that can be solubilized at high concentrations (10x to 100x) Concentrated culture medium formulations (2–10x) or 1x cell culture medium formulations can be prepared by mixing a sufficient amount of the concentrated subgroup solutions with each other and with a sufficient amount of a diluent (water, buffer, etc.).

Escalating demand for large volumes of nutrient medium and buffered salt solutions and increasing pressure to minimize batch-associated costs, such as sterile filtration and quality release testing, has driven a requirement for increased production batch sizes of liquid medium. As a result, stainless steel formulation tanks of 5000–10,000 liters for preparation of large batches of liquid medium or buffered salt solutions have become relatively common. However, scale-up manufacture of these fluids in this manner presents challenges regarding product quality and economy.

What is needed is a system and method for providing continuous, online preparation of large volumes of biological fluids (e.g., liquid medium, buffered salt solutions, etc.) within a highly controlled manufacturing system.

SUMMARY OF THE INVENTION

The present invention is a system and method for continuous, online preparation of cell culture medium formulations from selected subgroups of medium concentrates. In particular, a computer controlled system controls the flow of a diluent and one or more concentrated solutions into a static mixing chamber wherein the diluent and the concentrated solutions are mixed to form the cell culture medium formulations.

The present invention is able to formulate a cell culture medium from concentrated solution subgroups including an acid soluble concentrate solution subgroup, a group I salts solution concentrate subgroup, a group II salts solution concentrate subgroup, and a base soluble solution concentrate subgroup. Furthermore, the present invention is able to adjust the pH of the cell culture medium using either an acid solution or a base (caustic) solution.

In particular, the present invention is able to mix the concentrated solution subgroups with the diluent in a manner such that the ingredients of the concentrated solution subgroups do not adversely react chemically with one another.

One feature of the present invention is the preparation of large quantities of 1x cell culture medium (100,000 liters or more) while requiring only one quality control test. By increasing the size of the "batch," the present invention reduces the per liter cost of cell culture medium.

Another feature of the present invention is the increased consistency in the 1x cell culture medium. Statistical analyses have demonstrated that the present invention is able to provide 1x cell culture medium with homogeneity within batches of +2.0%. Furthermore, the present invention provides improved precision between production runs of 1x cell culture medium manufactured from identical concentrate solutions of +3.0%.

Still another feature of the present invention is a clean in place (CIP) and a steam in place (SIP) system which allows various components of the present invention to be sanitized and sterilized according to current good manufacturing practices (cGMP).

Further features and advantages of the present invention, as well as the structure and operation of various embodiments of the present invention, are described in detail below with reference to the accompanying drawings.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE PREFERRED EMBODIMENTS

Figure 1:
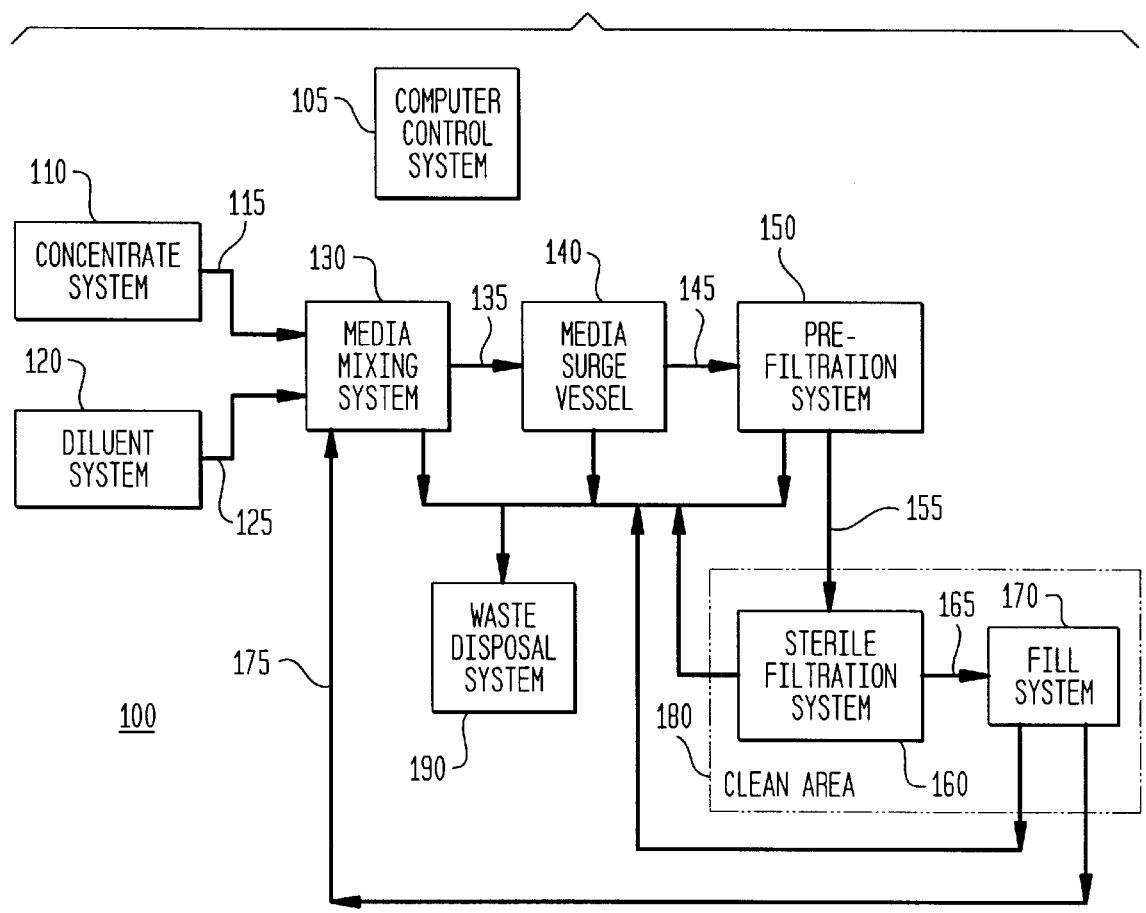
FIG. 1 illustrates an automated liquid manufacturing system (ALMS) according to the present invention.

In the description that follows, a number of terms conventionally used in the field of cell culture medium are utilized extensively. In order to provide a clear and consistent understanding of the specification and claims, and the scope to be given such terms, the following definitions are provided.

Ingredients. The term "ingredients" refers to any compound, whether of chemical or biological origin, that can be used in cell culture medium to maintain or promote the growth or proliferation of cells. The terms "component," "nutrient," and "ingredient" can be used interchangeably and are all meant to refer to such compounds. Typical ingredients that are used in cell culture medium formulations include amino acids, salts, metals, sugars, lipids, nucleic acids, hormones, vitamins, fatty acids, proteins and the like. Other ingredients that promote or maintain growth of cells in vitro can be selected by those of skill in the art, in accordance with the particular need.

Cell Culture. By "cell culture" is meant cells or tissues that are maintained, cultured or grown in an artificial, in vitro environment.

Culture Vessel. Glass, plastic or metal containers of various sizes that can provide an aseptic environment for growing cells are termed "culture vessels."

Cell Culture Medium. The phrases "cell culture medium" or "culture medium" or "medium formulation" or "cell culture medium formulation" refer to a nutritive solution for culturing or growing cells. The ingredients that comprise such medium formulations may vary depending on the type of cell to be cultured. In addition to nutrient composition, osmolarity and pH are considered important parameters of culture medium formulations.

Compatible Ingredients. Each ingredient used in cell culture medium formulations has unique physical and chemical characteristics. By "compatible ingredients" is meant those medium nutrients which can be maintained in solution and form a "stable" combination. A solution containing "compatible ingredients" is said to be "stable" when the ingredients do not degrade or decompose substantially into toxic compounds, or do not degrade or decompose substantially into compounds that can not be utilized or catabolized by the cell culture. Ingredients are also considered "stable" if degradation can not be detected or when degradation occurs at a slower rate when compared to decomposition of the same ingredient in a 1x cell culture medium formulation. Glutamine, for example, in 1x medium formulations, is known to degrade into pyrrolidone carboxylic acid and ammonia. Glutamine in combination with divalent cations are considered "compatible ingredients" since little or no decomposition can be detected over time.

Compatibility of medium ingredients, in addition to stability measurements, are also determined by the "solubility" of the ingredients in solution. The term "solubility" or "soluble" refers to the ability of an ingredient to form a solution with other ingredients. Ingredients are thus compatible if they can be maintained in solution without forming a measurable or detectable precipitate. Thus, the term "compatible ingredients" as used herein refers to the combination of particular culture medium ingredients which, when mixed in solution either as concentrated or 1x medium formulations, are "stable" and "soluble."Any combination of ingredients that is not compatible is said to be chemically incompatible.

1x Formulation. A cell culture medium is composed of a number of ingredients and these ingredients vary from medium to medium. A "1x formulation" or "1x medium formulation" is meant to refer to any aqueous solution that contains some or all ingredients found in a cell culture medium. The "1x formulation" can refer to, for example, the cell culture medium or to any subgroup of ingredients for that medium. The concentration of an ingredient in a 1x solution is about the same as the concentration of that ingredient found in the cell culture formulation used for maintaining or growing cells. Cell culture medium formulations used to grow cells are 1x formulation by definition. When a number of ingredients are present (as in a subgroup of compatible ingredients), each ingredient in a 1x formulation has a concentration about equal to the concentration of those ingredients in a cell culture medium. For example, RPMI 1640 culture medium contains, among other ingredients, 0.2 g/l L-arginine, 0.05 g/l L-asparagine, and 0.02 g/l L-aspartic acid. A "1x formulation" of these amino acids, which are compatible ingredients according to the present invention, contains about the same concentrations of these ingredients in solution. Thus, when referring to a "1x formulation," it is intended that each ingredient in solution has the same or about the same concentration as that found in the cell culture medium being described. The concentrations of medium ingredients in a 1x formulation are well known to those of ordinary skill in the art, See *Methods For Preparation of Media, Supplements and Substrate For Serum-Free Animal Cell Culture,* Allen R. Liss, N.Y. (1984), which is incorporated by reference herein in its entirety. The osmolarity and/or pH, however, may differ in a 1x formulation compared to the culture medium, particularly when fewer ingredients are contained by the 1x formulation.

10x Formulation. A "10x formulation" refers to a solution wherein each ingredient in that solution is about 10 times more concentrated than the same ingredient in the cell culture medium formulation. RPMI 1640 medium, for example, contains among other things, 0.3 g/l L-glutamine. By definition, a "10x formulation" contains about 3.0 g/l glutamine. A "10x formulation" may contain a number of additional ingredients at a concentration about 10 times that found in the 1x culture medium. As will be apparent, "25x formulation," "50x formulation" and "100x formulation" designate solutions that contain ingredients at about 25, 50 or 100 fold concentrations, respectively, as compared to a 1x cell culture medium. Again, the osmolarity and pH of the medium formulation and concentrated formulation may vary.

Automated Liquid Manufacturing System

According to the present invention, an automated liquid manufacturing system (ALMS) continuously prepares medium products (e.g., cell culture medium, buffered salt solutions, salt solutions, buffers, etc.) having various formulations (e.g., 1–10x) by mixing one or more concentrate solution subgroups together with a diluent (e.g. water, buffer, etc.). The amount of concentrated solution and amount of diluent needed may vary depending on the concentration of each subgroup, the number of subgroups, and the desired concentration of the final medium product. One of ordinary skill in the art can easily determined a sufficient volume of a diluent and a sufficient volume of the concentrated solutions to prepare the desired medium product.

The pH of the desired medium product may also be adjusted by the addition of acid or base. The medium product, however, may not require any adjustment, especially if the pH of the medium product as prepared is within the desired pH range. Osmolarity of the medium product can also be adjusted after mixing the concentrated solutions with the diluent. Typically, the desired osmolarity may be predetermined and adjustments in the salt concentration of the concentrated solutions may be made to prepare a final medium product with the desired osmolarity.

The present invention also provides for on-line sanitization and sterilization in place as required by current good manufacturing practices (cGMP). The sanitization operation is commonly referred to as "clean in place," and sterilization operation is commonly referred to as "steam in place." These operations are discussed in further detail below.

According to the present invention, sufficient amounts of each concentrate solution subgroup are continuously admixed with sufficient amounts of a diluent in a mixing chamber, while the resulting medium product is continuously removed. The following describes various aspects of the present invention and the manner in which they accomplish the continuous preparation of medium product.

FIG. 1 illustrates a system level block diagram of an automated liquid manufacturing system (ALMS) 100 according to the present invention. ALMS 100 includes a concentrate system 110, a diluent system 120, a medium mixing system 130, a medium surge vessel 140, a prefiltration system 150, a sterile filtration system 160 and a fill system 170. Sterile filtration system 160 and fill system 170 operate in a clean area 180. In addition to the above-mentioned system components, a preferred embodiment of the present invention includes a waste disposal system 190. Each of these components of ALMS 100 will be discussed in further detail below.

A preferred embodiment of the present invention is controlled by a computer control system 105. For ease of illustration, connections between computer control system 105 and the various components of ALMS 100 have not been shown. Needless to say, each of the components of ALMS 100 has some subcomponent, be it a valve, a pump, a sensor, etc., that is connected to computer control system 105 and used to control the operation of ALMS 100 as would be apparent. Computer control system 105 is described in further detail below.

Concentrate System

Concentrate system 110 provides one or more concentrate solutions 115 to ALMS 100. Specifically, concentrate system 110 provides concentrate solutions 115 to medium mixing system 130. Concentrate system 110 may perform this task in a variety of ways. In one embodiment of the present invention, concentrate system may provide concentrate solutions 115 in a manner similar to that described in commonly owned U.S. Pat. No. 5,474,931 issued to DiSorbo et al. on Dec. 12, 1995, which is incorporated herein by reference as if reproduced below in its entirety. DiSorbo discloses a method for producing liquid medium concentrates in compatible subgroups. According to this embodiment of the present invention, concentrate solutions 115 are chemically stable 50x formulations of liquid medium concentrates.

These subgroups include the following: an acid soluble concentrate solution subgroup, a group I salts concentrate solution subgroup, a group II concentrate solution subgroup, and a base soluble concentrate solution subgroup. In addition, sodium hydroxide may be prepared as a concentrate solution subgroup although this is not necessary. The acid soluble concentrate solution subgroup referred to herein is essentially equivalent to the acid-soluble subgroup referred to in DiSorbo; the group I salts concentrate solution subgroup referred to herein is essentially equivalent to the glutamine-containing subgroup referred to in DiSorbo; the group II salts concentrate solution subgroup referred to herein is essentially equivalent to the weak acid-base soluble subgroup referred to in DiSorbo; and the base soluble concentrate solution subgroup referred to herein is essentially equivalent to the alkali-soluble subgroup referred to in DiSorbo. The remaining subgroups referred to in DiSorbo are treated as reserve concentrate solutions for purposes of the present invention.

In this embodiment, the subgroups are formulated and "kited" according to published procedures as would be apparent. After being prepared according to these procedures the subgroups are stored in intermediate storage vessels for use by ALMS 100.

In another embodiment of the present invention, concentrate system 110 provides preformulated and prepackaged concentrate solutions 115. These concentrate solutions 115 are purchased from a manufacturer of such concentrate solutions such as are available from Life Technologies, Incorporated, 3175 Staley Road, Grand Island, N.Y., 716/

774–6700. In addition, concentrated subgroups for buffered salts can be obtained from Life Technologies as acid soluble concentrate solution subgroups and base soluble concentrate solution subgroups. This embodiment permits a manufacturer of medium products to purchase concentrate solutions 115 without itself having the facilities to manufacture or produce such concentrate solutions 115.

In yet another embodiment of the present invention, concentrate system 110 provides an on-line concentrate solution 115 as a part of a continuous manufacturing process in which concentrate solutions 115 are produced directly from raw materials and passed directly to ALMS 100 without an intermediate storage device such as that described in DiSorbo.

As would be apparent to one skilled in the art, other types of concentrate solutions 115 are available other than the subgroups described above. Furthermore, other means for providing concentrate solution 115 to ALMS 100 may be available as would also be apparent.

Diluent System

Diluent system 120 provides a diluent 125 to ALMS 100. In particular, diluent system 120 provides diluent 125 to medium mixing system 130. Diluent 125 may be any solution or liquid that may be used to dilute concentrate solutions 115. Such diluents include water, buffers, salt solutions, etc. In a preferred embodiment of the present invention, diluent 125 is water, most preferably, water for injection. However, any diluent 125 may be used in ALMS 100 that appropriately dilutes concentrate solutions 115 according to the particular needs of the medium product manufacturer.

Figure 2:
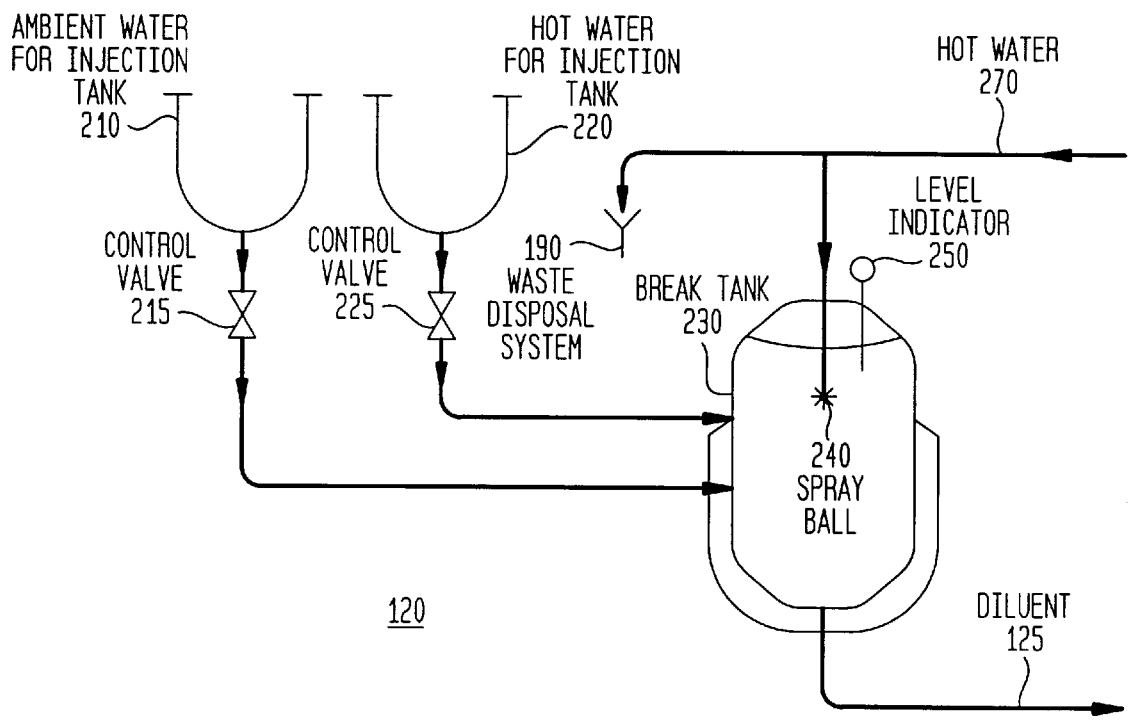
FIG. 2 illustrates a diluent system according to a preferred embodiment of the present invention.

A preferred embodiment of diluent system 120 is illustrated in FIG. 2. In this embodiment of the present invention, diluent system 120 includes an ambient water for injection (WFI) tank 210, a hot WFI tank 220, a control valve 215, a control valve 225, and a WFI break tank 230. WFI break tank 230 includes a level indicator 250 and a spray ball 240.

The purpose of WFI break tank 230 is to provide an atmospheric break between the plant water system and ALMS 100 as required by current good manufacturing practices (cGMP). In addition, WFI break tank 230 assures removal of entrained air from ambient WEI tank 210 and hot WFI tank 220 prior to their introduction to ALMS 100.

In one embodiment of the present invention, ambient WFI tank 210 is not a tank. Rather, ambient WFI tank 210 is directly connected to the plant's water system. In other embodiments of the present invention, ambient WFI tank 210 may actually be a tank. This may be the case, for example, when a diluent 125 other than water is used, or when a particular type of water is required (e.g. deionized, distilled, sterile, etc.). Hot WFI tank 220 provides hot water to ALMS 100 during a clean-in-place (CIP) operation which is discussed in further detail below.

Valve 215 and valve 225 control the flow of ambient water from ambient WFI tank 210 and hot water from hot WFI tank 220, respectively, to WFI break tank 230. In a preferred embodiment of the present invention, WFI break tank 230 provides ambient water as diluent 125 to ALMS 100.

Level indicator 250 monitors a level of diluent 125 in WFI break tank 230. Level indicator 250 is monitored by computer control system 105 to maintain an appropriate level of diluent 125 in WFI break tank 230.

Spray ball 240 is a part of the CIP operation which is discussed in further detail below. Spray ball 240 provides a mechanism for cleaning the inside of WFI break tank 230 during the CIP operation.

Medium Mixing System

Figure 3:
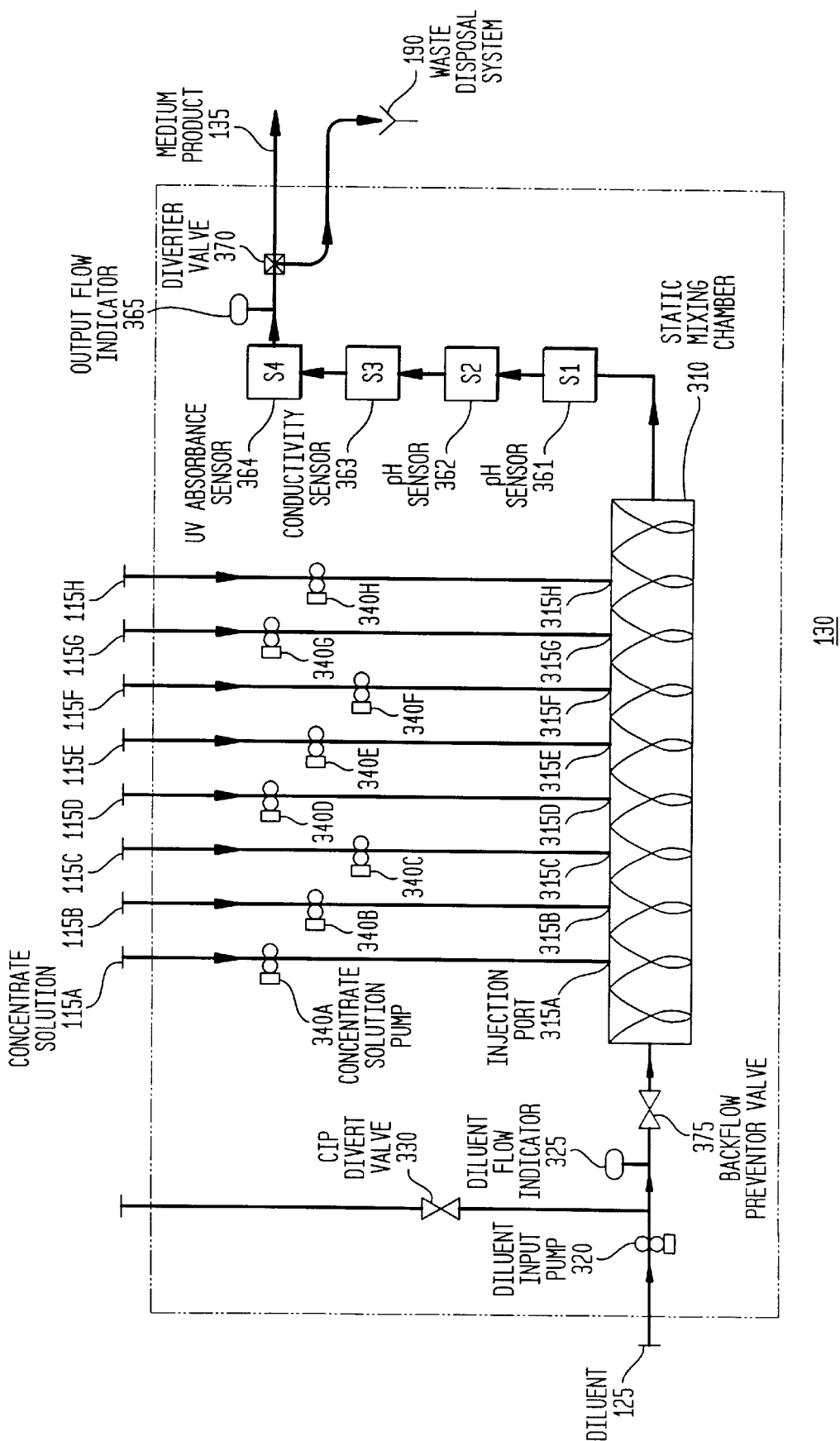
FIG. 3 illustrates a medium mixing system according to a preferred embodiment of the present invention.

Medium mixing system 130 is shown in further detail in FIG. 3. Medium mixing system 130 includes a static mixing chamber 310, a diluent input pump 320, a diluent flow indicator 325, a CIP divert valve 330, a series of concentrate solution pumps 340 (shown as concentrate solution pumps 340A–H), a first pH sensor 361, a second pH sensor 362, a conductivity sensor 363, a UV absorbance sensor 364, an output flow indicator 365, a diverter valve 370, and a back flow preventer valve 375. Each of these elements of medium mixing system 130 is described in further detail below.

Medium mixing system 130 receives diluent 125 and one or more concentrate solutions 115 and mixes them in mixing chamber 310. Medium mixing system 130 accomplishes this in a manner such that none of the ingredients of concentrate solutions 115 adversely chemically react with one another or with diluent 125. By "adversely chemically react" it is meant that the ingredients react 1) to form an irreversible precipitate; 2) to cause degradation in one or more components of the concentrate solutions; 3) to cause certain components to become inactivated; or 4) to cause any other condition that would result in a medium product 135 that fails to meet the requirements of a medium product user.

Diluent input pump 320 controls the flow of diluent 125 into static mixing chamber 310. This flow is measured by diluent flow indicator 325. Diluent flow indicator 325 permits computer control system 105 to monitor the flow of diluent 125 and thereby, control diluent input pump 320. Back flow preventer valve 375 prevents diluent 125 from flowing backwards from static mixing chamber Based on the flow of diluent 125 into static mixing chamber 310, computer control system 105 controls the flows of concentrate solutions 115 (shown as concentrate solutions 115A–H) into static mixing chamber 310 via concentrate solution pumps 340 (shown as concentrate solution pumps 340A–H). The flow of each of concentrate solutions 115A–H is controlled to be proportional to the flow of diluent 125 into static mixing chamber 310 according to a formulation of a desired medium product.

Sensors 361, 362, 363, 364 and 365 monitor a medium product 135 output from static mixing chamber 310 to ensure that particular parameters associated with medium product 135 are within acceptable levels associated with the desired medium product. These sensors are coupled to computer control system 105 which monitors these parameters of medium product 135 to ensure that proper mixing of concentrate solutions 115A–H and diluent 125 is being accomplished.

If the medium product is within the acceptance levels, medium product 135 passes to medium surge vessel 140. If not, computer control system 105 diverts medium product 135 to waste disposal system 190 via diverter valve 370. This allows medium mixing system 130 to guarantee an acceptable medium product 135. For example, when ALMS 100 starts up preparation of a particular medium product 135, the initial output of static mixing chamber 310 may not be within the acceptance levels for the particular medium product. Thus, this portion of the output is diverted to waste disposal system 190. When the output of static mixing chamber 310 enters into the acceptable levels (i.e., the operation reaches a "steady state"), the output from static mixing chamber 310 is passed to medium surge vessel 140.

In a preferred embodiment of the present invention, first pH sensor 361 and second pH sensor 362 are placed in close proximity to each other and as close to static mixing chamber 310 as possible, and prior to sensors 363, 364 to ensure that the proper pH levels of medium product 135 is being achieved.

Conductivity sensor 363 measures the ionic character of medium product 135. In particular, conductivity sensor 363 measures the resistivity of the flow of medium product 135. Conductivity sensor 363 is useful for determining the quality of medium product 135, especially for salt solutions.

UV absorbance sensor 364 measures an amount of ultraviolet light that passes through the flow of medium product 135. UV absorbance sensor 364 is useful for detecting the presence of precipitates within medium product 135. UV absorbance sensor 364 can also be used to measure a concentration of a particular component as an on-line measurement of concentrate addition and mixing quality.

As would be apparent to one skilled in the art, other types of sensors may be implemented in medium mixing system 130 to measure other levels of other parameters associated with medium product 135.

In a preferred embodiment of the present invention, concentrate solution pumps 340A–H are extremely precise variable speed pumps. In particular, concentrate solution pumps 340A–F are capable of delivering 0 to 3 liters of fluid per minute with +1.0% or better accuracy. Concentrate solution pumps 340G–H are capable of delivering 0 to 3.5 liters of fluid per minute with ±1.0% accuracy. A preferred embodiment of the present invention uses pumps which are manufactured by IVEK, North Springfield, Vt.

In a preferred embodiment of the present invention, concentrate solution 115A and concentrate solution 115B are reserved for providing an acid solution and a base solution, respectively, to static mixing chamber 310. Hence, referring to these as "concentrate solutions" may be considered a misnomer. However, as would be apparent, solutions, liquids, etc., other that "concentrate solutions" may be introduced in this manner to static mixing chamber 310 as would be apparent.

In this preferred embodiment of the present invention, acid solution 115A and caustic solution 115B adjust a pH level of diluent 125 according to specifications required by the production of medium product 135. The addition of either acid solution 115A or caustic solution 115B to diluent 125 is done first so that the proper pH level of diluent 125 can be achieved prior to the addition of other concentrate solutions 115C–H.

As shown in FIG. 3, diluent 125 enters static mixing chamber 310 and begins "mixing" sufficiently prior to the addition of any concentrate solutions 115A–H. This ensures that static mixing chamber 310 can provide a "turbulent diluent stream" from diluent 125 to enhance the overall mixing process between diluent steam 125 and concentrate solution 115A–H. The turbulent diluent stream is produced from diluent 125 by being forced past a series of baffles within static mixing chamber 310 as is well understood by those in the art. Also, the introduction of a last concentrate solution 115H occurs sufficiently prior to the end of static mixing chamber 310 so that last concentrate solution 115H can be sufficiently mixed in turbulent diluent stream. As discussed above, the output of static mixing chamber 310 is medium product 135.

Figure 6:
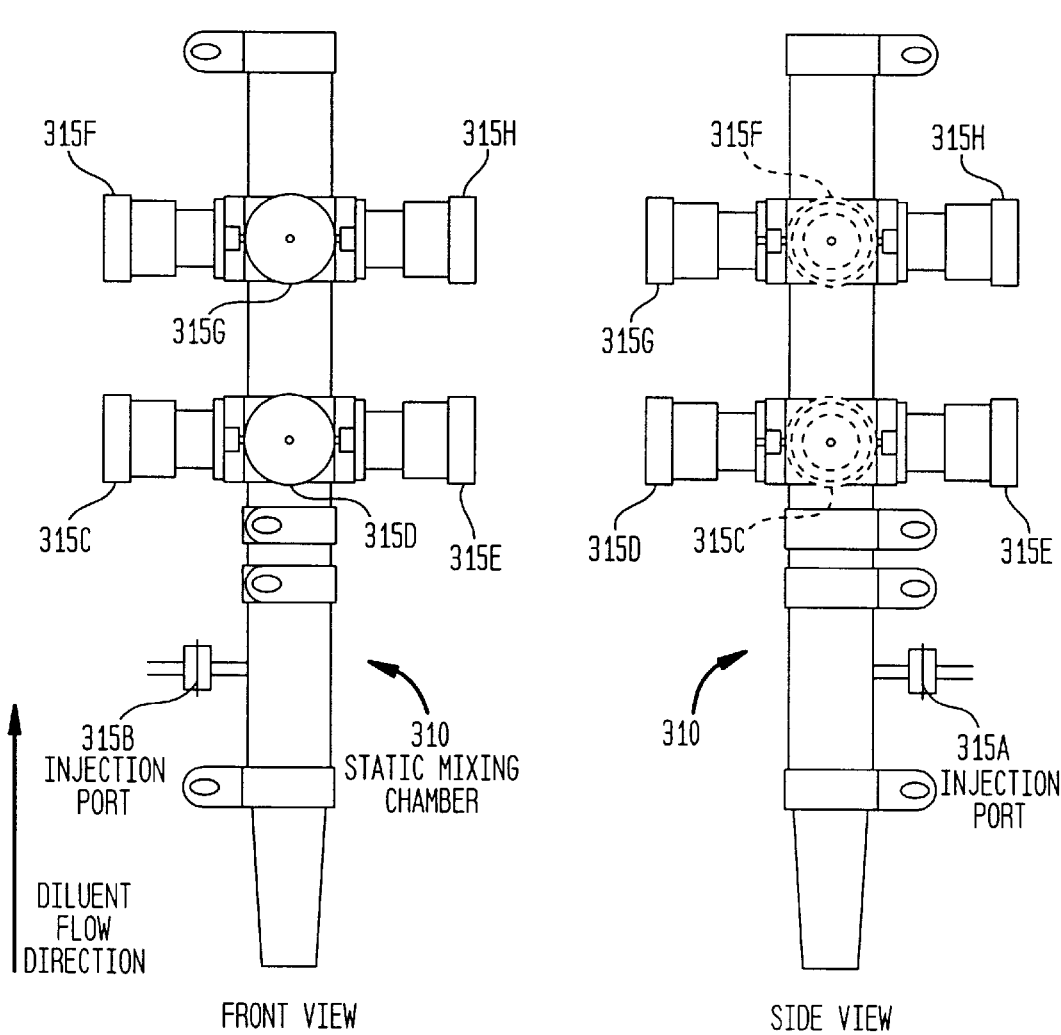
FIG. 6, respectively, illustrate a front view and a right side view of a medium mixing chamber according to a preferred embodiment of the present invention.

As shown in FIG. 3, static mixing chamber 310 includes a series of injection ports 315 (shown as injection ports 315A–315H). Injection ports 315 introduce concentrate solutions 115 into static mixing chamber 310. In particular, injection ports 315 introduce concentrate solutions 115 into turbulent diluent stream 125. FIG. 6 shows a mechanical drawing of static mixing chamber 310 in further detail.

Figure 7:
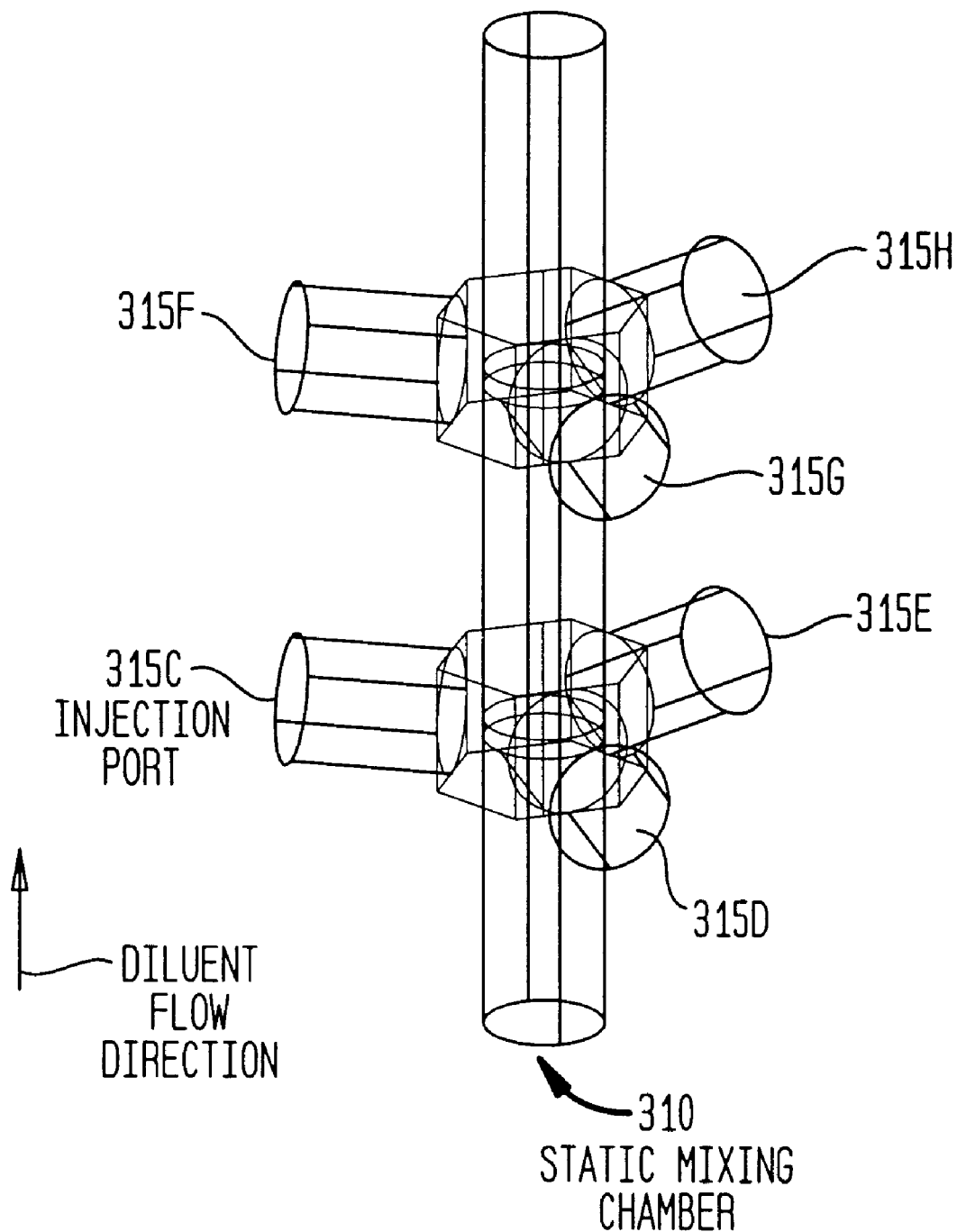
FIG. 7 illustrates an isometric view of a portion of the medium mixing chamber according to a preferred embodiment of the present invention.

FIG. 6A, FIG. 6B, and FIG. 7 illustrate static mixing chamber 310 in greater detail. In particular, FIGS. 6A and 6B are mechanical drawings showing a front view and a right side view, respectively, of static mixing chamber 310. FIG. 7 is an isometric drawing of static mixing chamber 310. As shown in FIGS. 6A, 6B, and 7, static mixing chamber 310 includes a series of injection ports 315. In particular, static mixing chamber 310 includes two groupings of radially disposed injection ports shown as injection ports 315C, 315D, and 315E and injection ports 315F, 315G, and 315H. In addition, as shown in FIGS. 6A and 6B, static mixing chamber 310 also includes two additional injection ports 315A and 315B.

Injection ports 315C, 315D, and 315E are described as being radially disposed around static mixing chamber 310. By "radially disposed" it is meant that injection ports 315C, 315D, and 315E are located on a common circumference around static mixing chamber 310. That is, injection ports 315C, 315D, and 315E are located at an approximately equal distance from the upstream end of static mixing chamber 310. Preferably, injection ports 315C, 315D, and 315E are spaced equally about the common circumference of static mixing chamber 310. Thus, for the case of three injection ports, the injection ports 315C, 315D, and 315E are space at 120 degree increments. Other embodiments may provide for non-equal spacings about the common circumference.

In one embodiment of the present invention, the injection ports are essentially disposed both "linearly" and "radially" from one another. Such would be the case, for example, where the injection ports were disposed in spiral fashion about static mixing chamber 310. Depending on the length of the spiral, the injection ports could be considered linearly disposed, radially disposed, or both.

Injection ports 315F, 315G, and 315H are also radially disposed around static mixing chamber 310. In addition, this group of injection ports, both individually and collectively, is "linearly disposed" along the fluid flow path of static mixing chamber 310 from injection ports 315C, 315D, and 315E as shown in FIG. 6. In other words, injection ports 315F, 315G, and 315H are located at an approximately equal distance from the upstream end of static mixing chamber 310, where this distance is sufficiently different from the distance from the upstream end of static mixing chamber 310 to injection ports 315C, 315D, and 315E.

In the particular embodiment shown in FIG. 6 and FIG. 7, three injection ports are radially disposed from one another in each of the two groups of injection ports. As would be apparent to one skilled in the art, additional injection ports may be included within each group, limited by two parameters. The first parameter is the number of injection ports that can physically, or mechanically, fit around static mixing chamber 310. The second parameter is the number of injection ports that can be used to introduce concentrate solutions 115 to diluent 125 without the ingredients of concentrate solutions 115 adversely chemically reacting with one another. As also would be apparent, fewer injection ports may be included within each group.

In addition to changing the number of injection ports within each radially disposed group, the number of radially disposed groups may also be changed. The number of radially disposed groups of injection ports is also limited by the same parameters as described above as would be apparent.

As shown in FIG. 6 and FIG. 7, diluent 125 flows from the upstream end of static mixing chamber 310 toward the downstream end of static mixing chamber 310. Thus, as diluent 125 flows through static mixing chamber 310, diluent 125 encounters injection ports 315A and 315B first, followed by injection ports 315C, 315D and 315E, and finally, injection ports 315F, 315G and 315H.

As thus described, static mixing chamber 310 provides two manners in which different concentrate solutions 115 can be added to diluent 125. The first manner is to add the different concentrate solutions 115 by using injection ports that are radially disposed from one another such as injection ports 315F, 315G, 315H or injection ports 315C, 315D and 315E. The second manner in which different concentrate solutions 115 can be added to diluent 125 is by using injection ports 315 that are linearly disposed from one another such as injection ports 315C and 315F. In either case, an injection port 315 adds a concentrate solution 115 to diluent 125 in a manner such that the concentrate solution 115 becomes sufficiently diluted by diluent 125 prior to encountering any other concentrate solution 115 added from a different injection port 315. This prevents any adverse chemical reaction between the ingredients of the two concentrate solutions.

While this is true in general, the order of introduction of certain concentrate solutions 115 to diluent 125 from a particular injection port configuration are preferred, while other orders of introduction are discouraged. For example, medium product 135 that includes a base soluble concentrate solution and a group II salts concentrate solution are preferably prepared by introducing these two concentrate solutions into diluent 125 by radially disposed injection ports. Doing so improves the microenvironment chemistry of the resulting medium product 135.

Also, medium product 135 that includes a group II salts concentrate solution and an acid soluble concentrate solution are preferably prepared by introducing these two concentrate solutions into diluent 125 from linearly disposed injection ports 315. Introducing these two concentrate solutions from injection ports that are radially disposed from one another is detrimental to product quality and may create an irreversible precipitation of critical cell culture medium components rendering the resulting medium product inactive.

In a preferred embodiment of the present invention, the following injection ports 315 concentrate solution 115 pairings are used: acid soluble concentrate solutions are introduced by injection port 315D; group I salts concentrate solutions are introduced by injection port 315E; group I salts concentrate solutions are introduced by injection port 315G; base soluble concentrate solutions are introduced by injection port 315H; acid solutions for adjusting pH are introduced by injection port 315A; and base (caustic) solutions for adjusting pH are introduced by injection port 315B. If sodium hydroxide concentrate solutions are used, they are preferably introduced by injection port 315F. Otherwise, injection port 315F is reserved for other concentrate solutions not included above. Injection port 315C is also reserved for other concentrate solutions not included above.

Medium Surge Vessel

Figure 4:
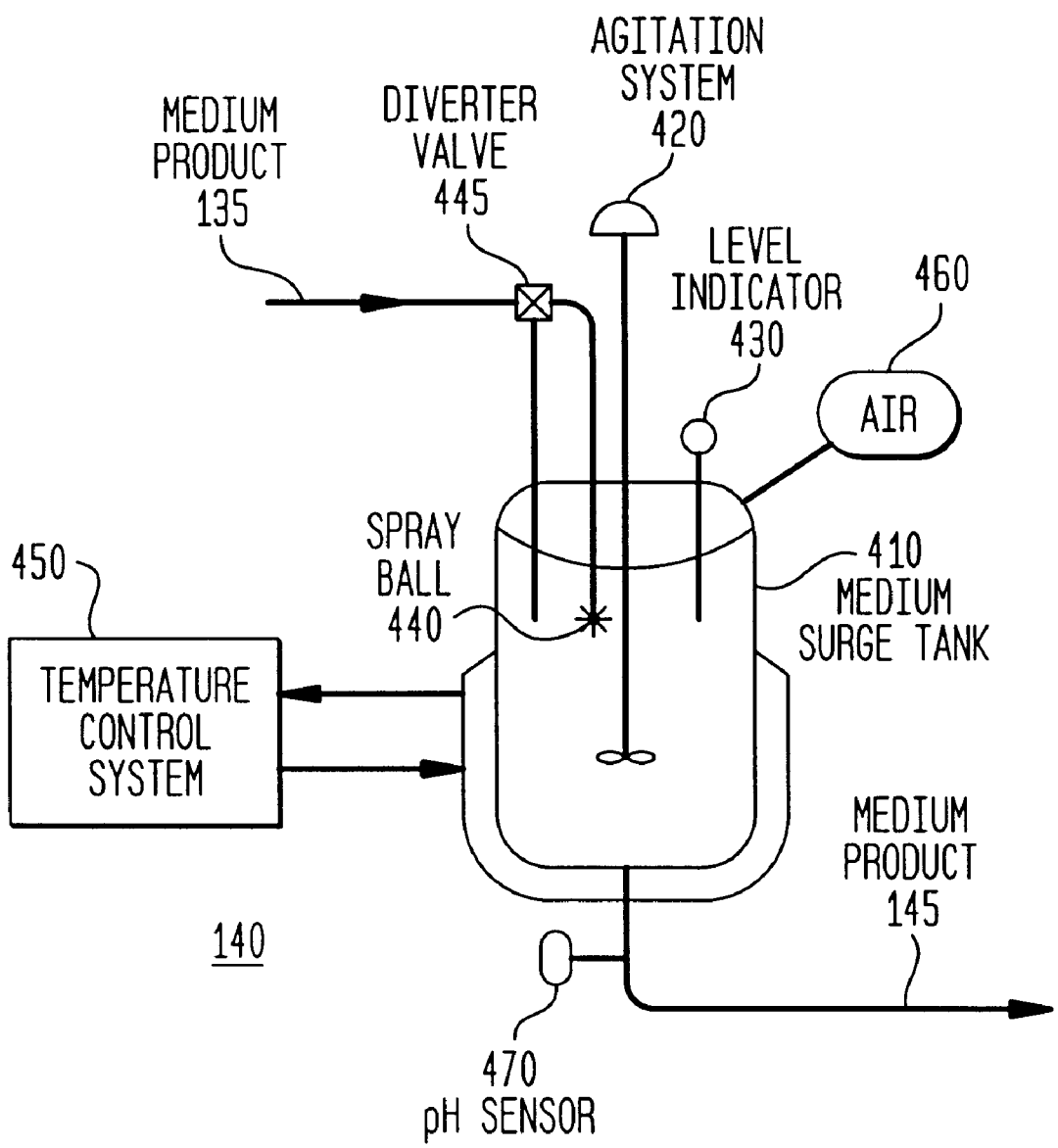
FIG. 4 illustrates a medium surge vessel according to one embodiment of the present invention.

FIG. 4 illustrates medium surge vessel 140 in greater detail. Medium surge vessel 140 includes a medium surge tank 410, an agitation system 420, a level indicator 430, a temperature control system 450, and a pH sensor 470. Medium product 135 from medium mixing system 130 enters medium surge tank 410 which provides a buffering mechanism for ALMS 100. In other words, medium surge vessel 140 provides a "buffer" between the continuous operation of medium mixing system 130 and the discontinuous operation of downstream components of ALMS 100 such as fill system 170. Thus, medium product 135 from medium mixing system is permitted to accumulate in medium surge vessel 140 when, for example, fill system 170 is temporarily shutdown to change fill containers.

An amount of medium product 135 in medium surge tank 410 is monitored by computer control system 105 via fill indicator 430. Depending on the level of medium product 135 in medium surge tank 410, computer control system 105 adjusts the output rate of medium product 135 from medium mixing system 130.

A pH level of medium product 135 is measured by pH sensor 470 as medium product 135 leaves medium surge tank 410. This permits computer control system 105 to monitor and ensure the quality of medium product 135.

In one embodiment of the present invention, agitation system 420 is used to provide agitation (i.e., mixing) to medium product 135 within medium surge tank 410. In one embodiment, agitation system 420 provides continuous mixing of medium product 135 in medium surge tank 410. In another embodiment, agitation system 420 provides mixing of medium product in medium surge tank 410 after a particular level is reached or some other parameter. Agitation system 420 may or may not be required in order to maintain medium product 135 in a homogeneous state In a preferred embodiment of the present invention, agitation system 420 is not used.

In one embodiment of the present invention, temperature control system 450 controls the temperature of medium product 135 within medium surge tank 410. Temperature control system 450 operates so as to maintain a particular temperature of medium product 135 in medium surge tank 410. Various means of controlling the temperature of the contents of medium surge tank 410 are available as would be apparent. In one embodiment of the present invention, glycol is circulated through an outer tank (not shown) around medium surge tank 410 thereby maintaining a particular temperature of the contents within medium surge tank 410. In a preferred embodiment of the present invention, temperature control system 450 is not used.

In one embodiment of the present invention, compressed air 460 is provided to medium surge tank 410 to maintain a given head pressure within medium surge tank 410. Compressed air 460 is used to provide sufficient pressure to move medium product 135 through medium surge tank into prefiltration system 150. In a preferred embodiment of the present invention, the head pressure is maintained between 6 and 10 p.s.i.g. Other embodiments may utilize gases other than air, such as nitrogen, to provide the head pressure as well as to prevent the outgasing from medium product 135 as would be apparent.

Diverter valve 445 is controlled by computer control system 105 to implement the CIP operation as will be discussed below. Diverter valve 445 diverts fluid to spray ball 440 in order to clean the inside of medium surge tank 410 during the CIP operation.

Filtration System

Figure 5:
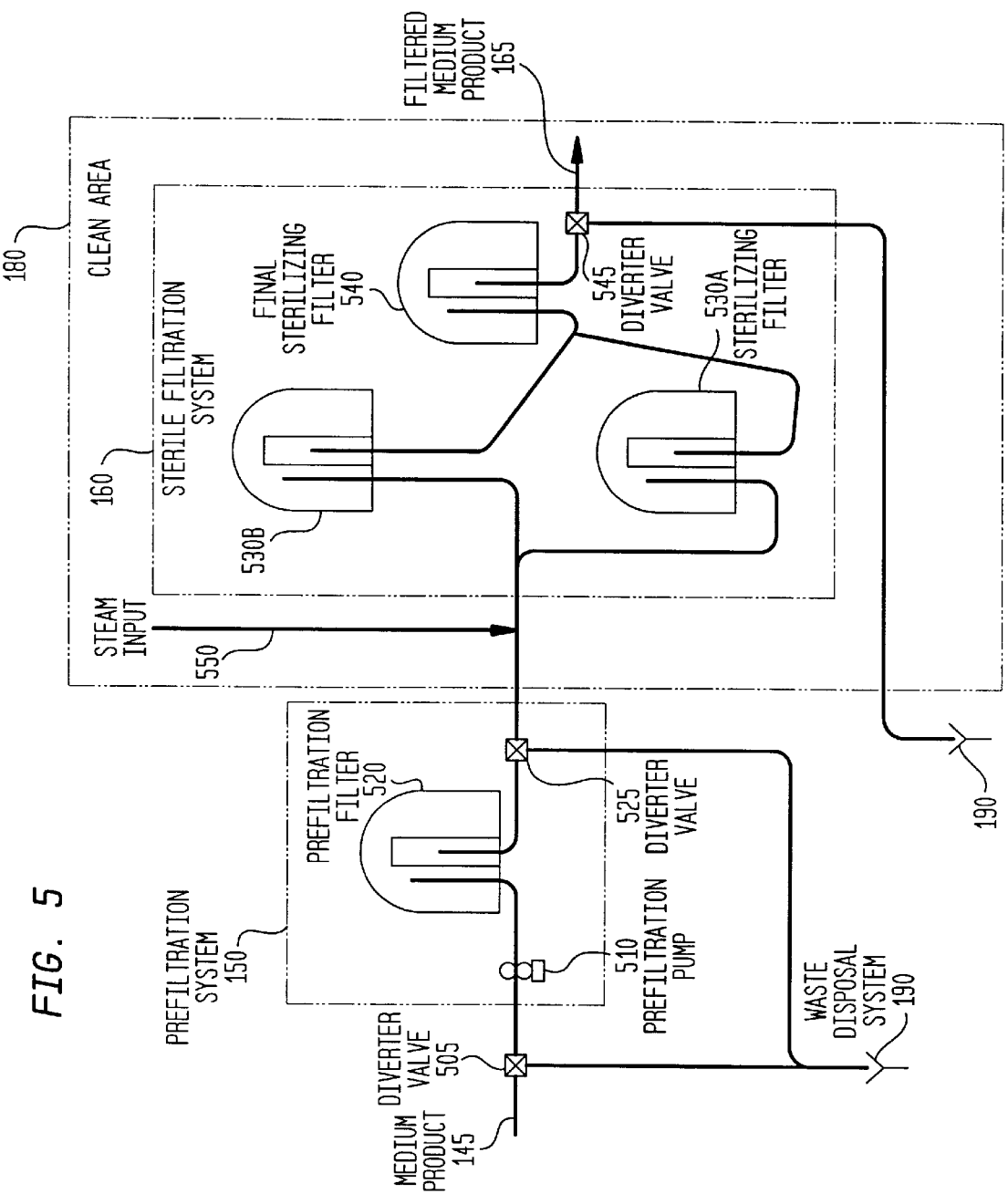
FIG. 5 illustrates a pre-filtration system and a sterile filtration system according to a preferred embodiment of the present invention.

FIG. 5 illustrates prefiltration system 150 and sterile filtration system 160 in further detail. Prefiltration system 150 includes a prefiltration pump 510 and a prefiltration filter 520. Prefiltration system 150 receives medium product 145 from medium surge tank 140. Prefiltration pump 510 pumps medium product 145 through a non-sterile prefilter filter 520. Prefilter filter 520 is a filter membrane that provides variable filtration of medium product 145. Depending upon the particular medium product 145 being prepared, the filter membrane is selected to filter particles that may range between 0.1 and 2 microns.

Medium product that has been filtered by prefiltration system 150 enters sterile filtration system 160. As shown in FIG. 5, sterile filtration system 160 operates in a clean area 180. Sterile filtration system 160 includes two sterilizing filters 530A and 530B in a parallel configuration followed by a final sterilizing filter 540. This particular configuration of sterilizing filters provides redundant 0.1 or 0.2 micron filtration for medium product 145. Filtered medium product 165 is output from sterile filtration system 160 and enters fill system 170.

Sterilizing filters 530 and final sterilizing filter 540 are steam sterilized via a steam in place operation which is discussed in further detail below. In a preferred embodiment, the sterilizing filters are steam sterilized prior to manufacturing a new batch of cell culture medium formulation.

Fill System

As shown, fill system 170 is also contained within clean area 180. Fill system 170 provides aseptic connections in clean area 180 so that multiple medium product containers can be filled outside of clean area 180.

In one embodiment of present invention, fill system 170 provides a mechanism whereby multiple containers (i.e., sterile bags, carboys, glass bottles, drums, etc.) can be filled. In another embodiment of the present invention, fill system 170 may not be required or may be modified. For example, an embodiment of ALMS 100 may be implemented to provide medium product 145 directly to a bioreactor as would be apparent.

Diverter valves 505, 525 and 545 are controlled by computer control system 105 and used during the CIP operation as will be discussed below. The diverter valves provide a mechanism to flush unwanted medium product through to waste disposal system 190 as well as to provide mechanisms to clean and product purge prefilter 520 and sterilizing filters 530A, 530B and 540.

ALMS Process Capability

In a preferred embodiment of the present invention, ALMS 100 is designed to operate with flow rates between 1,000 and 3,000 liters or medium product per hour. Other embodiments of the present invention may have different flow rates depending upon the sizing and accuracy of, for example, concentrate solution pumps 340, diluent input pump 320, and static mixing chamber 310.

In a preferred embodiment of the present invention, medium product 165 has an intra-run homogeneity with a precision tolerance of ±2.0%. Precision between production runs of medium product 165 from identical concentrated materials is ±3.0%. Furthermore, a pH fluctuation of medium product 165 is within ±0.1 units.

Clean In Process (CIP) and Steam In Place (SIP) Process Operations

ALMS 100 is designed for on-line sanitization and sterilization in place as required. The sanitization operation is commonly referred to as "clean in place." The sterilization operation using steam under pressure is commonly referred to as "steam in place." A typical operation will require sanitization of the entire system including WFI brake tank 230 and steam sterilization of sterile filtration system 160 as well as fill system 170.

Sanitization of ALMS 100 includes the flushing of the entire ALMS 100 with hot water from hot WFI 220. Hot water from hot WFI 220 is routed through ALMS 100 via diverter valves (e.g., diverter valve 145, diverter valve 505, diverter valve 525, diverter valve 545, etc.) to and through spray balls (e.g., spray ball 240 and spray ball 440), and recirculated from fill system 170 to media mixing system 130 via an appropriate conduit (shown as line 175 in FIG. 1) to flush ALMS 100. In one embodiment of the present invention, caustic solution is added to hot water from hot WFI 220 via static mixing chamber 310 to provide a hot caustic sanitization of ALMS 100. The hot caustic is recirculated, neutralized with acid and sent to waste disposal system 190.

For sterilizing ALMS 100, steam is introduced at the sterile filtration system 160 via a steam input port 550 located inside clean area 180. Steam flows through sterile filtration system 160, including sterilizing filters 530 and final sterilizing filter 540, and fill system 170, and heats these components to sterilization temperatures. The temperature is monitored at appropriate points and sterilization is confirmed using well known time/temperature parameters as would be apparent.

The by-products of the sanitization process are routed to waste disposal system 190 as shown in various figures. In one embodiment of the present invention, waste disposal system treats any by-products of ALMS 100 by appropriate measures so as not to introduce any harmful products into the plant's waste disposal system as would be apparent.

Computer Control System

Figure 8:
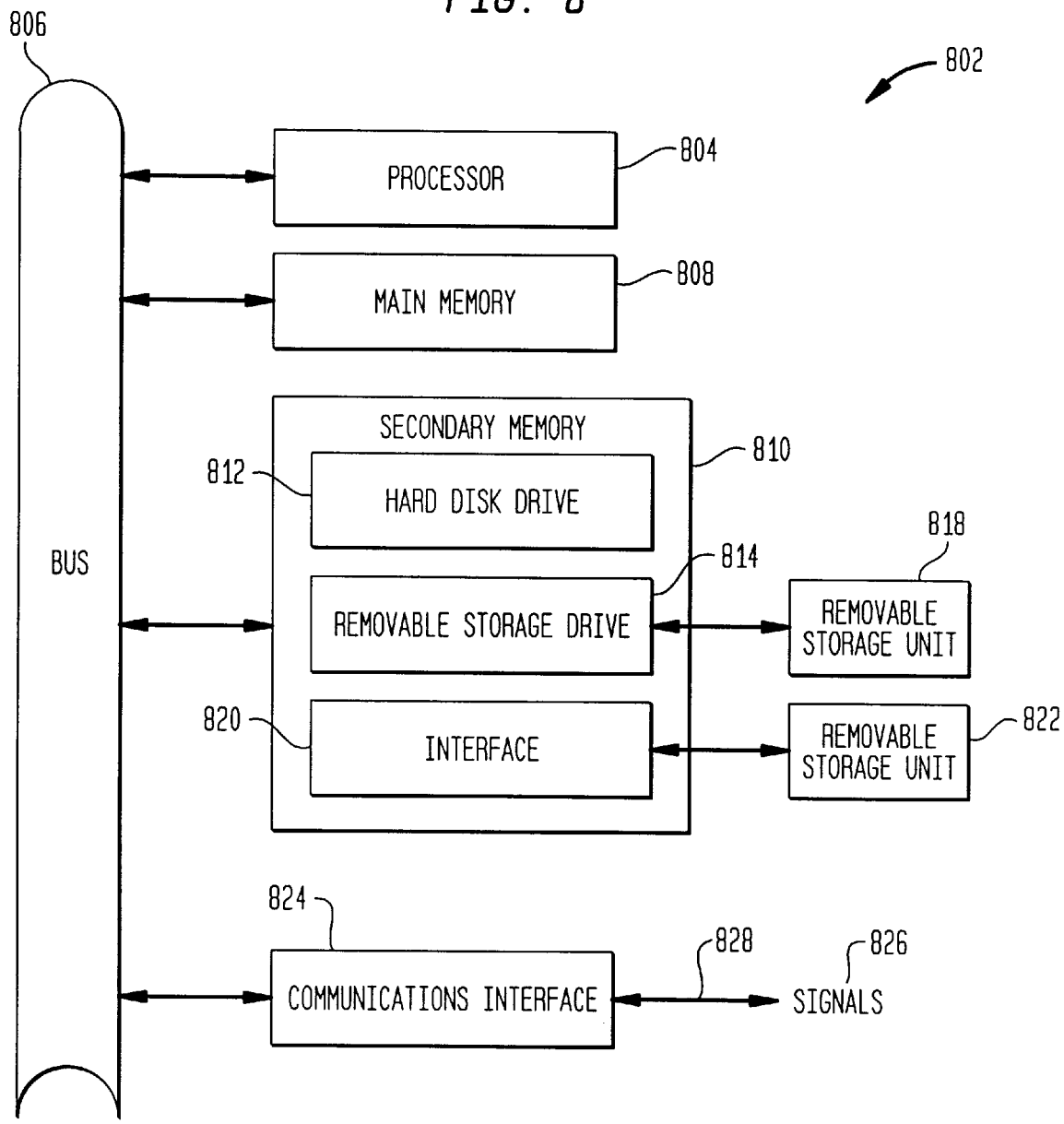
FIG. 8 illustrates an example of a computer control system useful for controlling the operation of the present invention.

In various embodiments of the present invention, computer control system 105 is implemented using hardware, software or a combination thereof and may be implemented in a computer system or other processing system. In fact, in one embodiment, the invention is directed toward a computer system capable of carrying out the functionality described herein. An example computer system 802 is shown in FIG. 8. Computer system 802 includes one or more processors, such as processor 804. Processor 804 is connected to a communication bus 806. Various software embodiments are described in terms of this example computer system. After reading this description, it will become apparent to a person skilled in the relevant art how to implement the invention using other computer systems and/or computer architectures.

Computer system 802 also includes a main memory 808, preferably random access memory (RAM), and may also include a secondary memory 810. Secondary memory 810 may include, for example, a hard disk drive 812 and/or a removable storage drive 814, representing a floppy disk drive, a magnetic tape drive, an optical disk drive, etc. Removable storage drive 814 reads from and/or writes to a removable storage unit 818 in a well known manner. Removable storage unit 818, represents a floppy disk, magnetic tape, optical disk, etc. which is read by and written to by removable storage drive 814. As will be appreciated, removable storage unit 818 includes a computer usable storage medium having stored therein computer software and/or data.

In alternative embodiments, secondary memory 810 may include other similar means for allowing computer programs or other instructions to be loaded into computer system 802. Such means can include, for example, a removable storage unit 822 and an interface 820. Examples of such can include a program cartridge and cartridge interface (such as that found in video game devices), a removable memory chip (such as an EPROM, or PROM) and associated socket, and other removable storage units 822 and interfaces 820 which allow software and data to be transferred from the removable storage unit 818 to computer system 802.

Computer system 802 can also include a communications interface 824. Communications interface 824 allows software and data to be transferred between computer system 802 and external devices. Examples of communications interface 824 can include a modem, a network interface (such as an Ethernet card), a communications port, a PCMCIA slot and card, etc. Software and data transferred via communications interface 824 are in the form of signals which can be electronic, electromagnetic, optical or other signals capable of being received by communications interface 824. Signals 826 are provided to communications interface via a channel 828. Channel 828 carries signals 826 and can be implemented using wire or cable, fiber optics, a phone line, a cellular phone link, an RF link and other communications channels.

In this document, the terms "computer program medium" and "computer usable medium" are used to generally refer to media such as removable storage device 818, a hard disk installed in hard disk drive 812, and signals 826. These computer program products are means for providing software to computer system 802.

Computer programs (also called computer control logic) are stored in main memory and/or secondary memory 810. Computer programs can also be received via communications interface 824. Such computer programs, when executed, enable the computer system 802 to perform the features of the present invention as discussed herein. In particular, the computer programs, when executed, enable processor 804 to perform the features of the present invention. Accordingly, such computer programs represent controllers of the computer system 802.

In an embodiment where the invention is implement using software, the software may be stored in a computer program product and loaded into computer system 802 using removable storage drive 814, hard drive 812 or communications interface 824. The control logic (software), when executed by processor 804, causes processor 804 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Conclusion

While the invention has been particularly shown and described with reference to several preferred embodiments thereof, it will be understood by those skilled in the art that various changes in form and details may be made therein without departing from the spirit and scope of the invention as defined in the appended claims.

What is claimed is:

1. An apparatus for continuously mixing aqueous solutions comprising:
    a static mixing chamber, having an upstream end and a downstream end for creating a turbulent diluent stream from a diluent introduced from said upstream end of said static mixing chamber; and
    a plurality of injection ports connected to a respective plurality of sources of chemically incompatible concentrate solutions, incorporated into said static mixing chamber, for introducing a plurality of said chemically incompatible concentrate solutions to said turbulent diluent stream such that where any two injection ports introduce chemically incompatible concentrate solutions, said two injection ports are sufficiently far apart that none of the ingredients of said chemically incompatible concentrate solutions introduced by said two injection ports adversely chemically react with each other, thereby forming a diluted mixture of said concentrate solutions at said downstream end of said static mixing chamber.

2. The apparatus of claim 1, wherein said plurality of injection ports comprise a plurality of injection ports that are radially disposed from one another.

3. The apparatus of claim 1, wherein said plurality of injection ports comprise a plurality of injection ports that are linearly disposed from one another.

4. The apparatus of claim 1, wherein said plurality of injection ports includes:
    a first plurality of injection ports that are radially disposed from one another; and
    at least one injection port that is linearly disposed from said first plurality of injection ports.

5. The apparatus of claim 4, wherein one of said first plurality of injection ports is connected to a source of a base soluble concentration solution and introduces said base soluble concentrate solution to said turbulent diluent stream.

6. The apparatus of claim 4, wherein one of said first plurality of injection ports is connected to a source of acid soluble concentrate solution and introduces said acid soluble concentrate solution to said turbulent diluent stream.

7. The apparatus of claim 4, wherein one of said first plurality of injection ports is connected to a source of group I salts concentrate solution and introduces said group I salts concentrate solution to said turbulent diluent stream.

8. The apparatus of claim 4, wherein one of said first plurality of injection ports is connected to a source of group II salts concentrate solution and introduces said group II salts concentrate solution to said turbulent diluent stream.

9. The apparatus of claim 4, wherein said at least one injection port is connected to a source of a concentrate solution and introduces said concentrate solution into said turbulent diluent stream.

10. The apparatus of claim 4, wherein said at least one injection port is connected to a source of a concentrate solution and introduces said concentrate solution into said turbulent diluent stream prior to said first plurality of injection ports introducing any concentrate solutions into said turbulent diluent stream.

11. The apparatus of claim 10, wherein said at least one injection port is connected to a source of an acid solution and introduces said acid solution into said turbulent diluent stream.

12. The apparatus of claim 10, wherein one of said at least one injection port is connected to a source of caustic solution and introduces said caustic solution into said turbulent diluent stream.

13. The apparatus of claim 4, wherein said first plurality of injection ports do not introduce both a group II salts concentrate solution and an acid soluble concentrate solution into said turbulent diluent stream.

14. The apparatus of claim 1, wherein said plurality of injection ports includes:
    a first plurality of injection ports incorporated into said static mixing chamber and radially disposed from one another;
    a second plurality of injection ports incorporated into said static mixing chamber, radially disposed from one another, and linearly disposed from said first plurality of injection ports; and
    at least one injection port incorporated into said static mixing chamber, linearly disposed from both said first plurality of injection ports and said second plurality of injection ports.

15. The apparatus of claim 14, wherein one of said first plurality of injection ports is connected to a source of a base concentrate solution and introduces said base soluble concentrate solution to said turbulent diluent stream.

16. The apparatus of claim 14, wherein one of said first plurality of injection ports is connected to a source of an acid soluble concentrate solution and introduces said acid soluble concentrate solution to said turbulent diluent stream.

17. The apparatus of claim 14, wherein one of said first plurality of injection ports is connected to a source of group I salts concentrate solution and introduces said group I salts concentrate solution to said turbulent diluent stream.

18. The apparatus of claim 14, wherein one of said first plurality of injection ports is connected to a source of group II salts concentrate solution and introduces said group II salts concentrate solution to said turbulent diluent stream.

19. The apparatus of claim 14, wherein said at least one injection port is connected to a source of a concentrate solution and introduces said concentrate solution into said turbulent diluent stream prior to any of said first plurality of injection ports introducing a concentrate solution into said turbulent diluent stream.

20. The apparatus of claim 14, wherein said at least one injection port is connected to a source of a concentrate solution and introduces said concentrate solution into said turbulent diluent stream.

21. The apparatus of claim 20, wherein said at least one injection port is connected to a source of an acid solution and introduces said acid solution into said turbulent diluent stream.

22. The apparatus of claim 20, wherein one of said at least one injection port is connected to a source of a caustic solution and introduces said caustic solution into said turbulent diluent stream.

23. The apparatus of claim 14, wherein said first plurality of injection ports do not introduce both a group II salts concentrate solution and an acid soluble concentrate solution into said turbulent diluent stream.

24. The apparatus of claim 14, wherein said second plurality of injection ports do not introduce both a group II salts concentrate solution and an acid soluble concentrate solution into said turbulent diluent stream.

25. The apparatus of claim 14, wherein one of said first plurality of injection ports is connected to a source of a base soluble concentrate solution and introduces said base soluble concentrate solution into said turbulent diluent stream and one of said second plurality of injection ports is connected to a source of a group II salt concentrate solution and introduces said group II salt concentrate solution into said turbulent diluent stream.

* * * * *